United States Patent
Deng et al.

(10) Patent No.: US 11,141,506 B2
(45) Date of Patent: Oct. 12, 2021

(54) ELECTRIFIED COMPOSITE MEMBRANE WITH EXTRACELLULAR MATRIX ELECTRICAL TOPOLOGY CHARACTERISTICS, AND PREPARATION METHOD THEREOF

(71) Applicant: PEKING UNIVERSITY SCHOOL AND HOSPITAL OF STOMATOLOGY, Beijing (CN)

(72) Inventors: Xuliang Deng, Beijing (CN); Yunyang Bai, Beijing (CN); Xuehui Zhang, Beijing (CN)

(73) Assignee: PEKING UNIVERSITY SCHOOL AND HOSPITAL OF STOMATOLOGY, Beijing (CN)

( * ) Notice: Subject to any disclaimer, the term of this patent is extended or adjusted under 35 U.S.C. 154(b) by 55 days.

(21) Appl. No.: 16/348,099

(22) PCT Filed: Aug. 10, 2018

(86) PCT No.: PCT/CN2018/099828
§ 371 (c)(1),
(2) Date: May 7, 2019

(87) PCT Pub. No.: WO2019/192116
PCT Pub. Date: Oct. 10, 2019

(65) Prior Publication Data
US 2020/0261621 A1    Aug. 20, 2020

(30) Foreign Application Priority Data
Apr. 3, 2018  (CN) .......................... 201810288369.5

(51) Int. Cl.
*A61L 27/44* (2006.01)
*A61F 2/28* (2006.01)
*A61L 27/50* (2006.01)

(52) U.S. Cl.
CPC .......... *A61L 27/446* (2013.01); *A61F 2/2875* (2013.01); *A61L 27/50* (2013.01); *A61F 2240/001* (2013.01); *A61L 2430/02* (2013.01)

(58) Field of Classification Search
CPC ................................. D01D 5/00; A61L 27/446
See application file for complete search history.

(56) References Cited

U.S. PATENT DOCUMENTS 9,180,166 B2 * 11/2015 Arinzeh ............... A61L 27/3834
9,181,636 B2 * 11/2015 Arinzeh ................... A61L 27/46
(Continued)

FOREIGN PATENT DOCUMENTS

| CN | 104208754 A | 12/2014 |
|---|---|---|
| CN | 106751250 A | 5/2017 |

(Continued)

OTHER PUBLICATIONS

Song et al., Enhanced dielectric and ferroelectric properties induced by dopamine-modified BaTiO3 nanofibers in flexible poly(vinylidene fluoride-trifluroetheylene) nanocomposites, 2012, Royal Society of Chemistry, J. Mater. Chem,, 2012, 22, pp. 8063-8068 (Year: 2012).*

(Continued)

*Primary Examiner* — Matthew J Daniels
*Assistant Examiner* — Andrew D Graham
(74) *Attorney, Agent, or Firm* — Platinum Intellectual Property LLP

(57) ABSTRACT

The invention involves a kind of electrified composite membrane with extracellular matrix electrical topology characteristics and its preparation method, which resolves the technical problems of poor matching of electric characteristics and natural extracellular matrix characteristics in the existing materials and limited restoration effect of materials. The invention provides a kind of electrified composite membrane with extracellular matrix electrical topology (Continued)

characteristics mainly composed of ferroelectric polymer matrix and piezoelectric active fiber fillings. By regulating the draw ratio, content and of piezoelectric active fiber and thickness of composite film, the invention can realized the flexibility of film material and electrical topological features of bionic extracellular matrix, with proper tissue adhesion and good electric adaptability and high clinical operability.

4 Claims, 4 Drawing Sheets

(56) References Cited

U.S. PATENT DOCUMENTS

| | | | |
|---|---|---|---|
| 9,192,655 B2* | 11/2015 | Arinzeh | A61K 38/39 |
| 2003/0215624 A1* | 11/2003 | Layman | D01F 6/30 428/221 |
| 2004/0018226 A1* | 1/2004 | Wnek | D01D 5/0038 424/443 |
| 2006/0057375 A1* | 3/2006 | Harren | D01D 5/00 428/364 |
| 2006/0204539 A1* | 9/2006 | Atala | D01D 5/0007 424/423 |
| 2007/0232698 A1* | 10/2007 | Shibuya | A61K 31/195 514/561 |
| 2008/0193531 A1* | 8/2008 | Hermelin | A61P 3/12 424/474 |
| 2008/0199698 A1* | 8/2008 | Kohinata | D01F 6/92 428/401 |
| 2008/0207798 A1* | 8/2008 | Hellring | D01F 6/44 523/222 |
| 2008/0294089 A1* | 11/2008 | Hardy | A61K 47/6911 604/22 |
| 2009/0148701 A1* | 6/2009 | Wendorff | D01D 5/003 428/401 |
| 2009/0234459 A1* | 9/2009 | Sporring | A61F 2/30721 623/18.11 |
| 2009/0253328 A1* | 10/2009 | Watanabe | D01F 1/10 442/327 |
| 2009/0317446 A1* | 12/2009 | Tan | A61L 27/3821 424/423 |
| 2009/0326128 A1* | 12/2009 | Macossay-Torres | B82Y 30/00 524/413 |
| 2010/0021794 A1* | 1/2010 | Kim | B01J 23/38 429/509 |
| 2010/0099640 A1* | 4/2010 | Geuns | C07H 15/18 514/34 |
| 2010/0120315 A1* | 5/2010 | Imashiro | D01D 5/003 442/351 |
| 2010/0127219 A1* | 5/2010 | Mohamed | C09J 175/16 252/500 |
| 2010/0151311 A1* | 6/2010 | Usami | B32B 27/20 429/145 |
| 2010/0167078 A1* | 7/2010 | Kim | C01G 55/00 428/546 |
| 2010/0178830 A1* | 7/2010 | Nakamori | D01D 5/0038 442/351 |
| 2010/0197651 A1* | 8/2010 | Taniguchi | A61P 3/04 514/210.02 |
| 2010/0241071 A1* | 9/2010 | Atanasoska | A61L 27/446 604/103.02 |
| 2011/0018174 A1* | 1/2011 | Baca | B29C 48/04 264/465 |
| 2011/0033540 A1* | 2/2011 | Daniloff | A61L 27/52 424/484 |
| 2011/0049769 A1* | 3/2011 | Duchoslav | D01D 10/02 264/484 |
| 2011/0068493 A1* | 3/2011 | Buyuktanir | C09K 19/544 264/1.27 |
| 2011/0260584 A1* | 10/2011 | Yu | H01L 41/082 310/339 |
| 2011/0301696 A1* | 12/2011 | Mangiardi | A61L 31/10 623/1.46 |
| 2011/0305872 A1* | 12/2011 | Li | A61L 29/06 428/141 |
| 2011/0305898 A1* | 12/2011 | Zhang | B32B 27/28 428/336 |
| 2012/0004370 A1* | 1/2012 | Scott | B05B 5/0255 525/106 |
| 2012/0045487 A1* | 2/2012 | Lahann | A61P 5/36 424/400 |
| 2012/0178332 A1* | 7/2012 | Uchida | C08L 77/10 442/351 |
| 2012/0244095 A1* | 9/2012 | Konradi | A01N 43/50 424/61 |
| 2012/0282484 A1* | 11/2012 | Joo | C04B 35/6365 428/606 |
| 2013/0146810 A1* | 6/2013 | Zhang | D01F 6/16 252/194 |
| 2014/0141152 A1* | 5/2014 | Sostek | D04H 1/4382 427/2.24 |
| 2014/0332733 A1* | 11/2014 | Joo | D01D 5/0015 252/513 |
| 2015/0044464 A1* | 2/2015 | Joo | D01F 6/14 428/375 |
| 2015/0056471 A1* | 2/2015 | Joo | C04B 35/6224 428/687 |
| 2015/0247263 A1* | 9/2015 | Joo | D01D 5/0015 252/71 |
| 2016/0074555 A1* | 3/2016 | Kaikkonen | A61M 5/31596 604/82 |
| 2016/0115128 A1* | 4/2016 | Aida | C07D 401/14 514/210.2 |
| 2016/0168755 A1* | 6/2016 | Toyoda | D01D 5/0092 536/123.12 |
| 2017/0007739 A1* | 1/2017 | Reves | A61L 27/10 |
| 2018/0086874 A1* | 3/2018 | Hattori | D01D 5/003 |
| 2018/0155333 A1* | 6/2018 | Kamei | C07D 417/14 |
| 2019/0071534 A1* | 3/2019 | Hattori | C08G 18/4009 |

FOREIGN PATENT DOCUMENTS

| | | |
|---|---|---|
| CN | 107233625 A | 10/2017 |
| CN | 107261205 A | 10/2017 |
| WO | 03045461 A1 | 6/2003 |

OTHER PUBLICATIONS

Chen et al., Normal and Abnormal Grain Growths in BaTiO3 Fibers, 2014, The American Ceramic Society, J. Am. Ceram. Soc. 2014, 97 [9], pp. 2755-2761 (Year: 2014).*

* cited by examiner

ELECTRIFIED COMPOSITE MEMBRANE WITH EXTRACELLULAR MATRIX ELECTRICAL TOPOLOGY CHARACTERISTICS, AND PREPARATION METHOD THEREOF

RELATED APPLICATIONS

This application is a United States National Stage Application filed under 35 U.S.C 371 of PCT Patent Application Serial No. PCT/CN2018/099828, filed Aug. 10, 2018, which claims Chinese Patent Application Serial No. CN 2018102883695, filed Apr. 3, 2018, the disclosure of all of which are hereby incorporated by reference in their entirety.

TECHNICAL FIELD

The invention involves the technical field of restoration materials for orthopedics and oral surgery, especially involves a kind of electrified composite membrane with extracellular matrix electrical topology characteristics and its preparation method.

BACKGROUND TECHNOLOGY

Implant restoration is currently the major means for treatment of large-area tissue defects. Due to their wide sources, controllable performance and low cost, artificial restoration materials are widely concerned among the tissue restoration materials. According to the bionic principle, skin wound healing, neurorestoration and bone defect repair are all observed with injury potential. A large number of studies prove that injury potential plays an important role in tissue restoration. Therefore, with respect of tissue restoration materials, electriferous materials will be beneficial to promote the quick healing of tissues and functional restoration. In recent years, electroactive materials become the hot point and trend of research as well as the new conception of tissue restoration material design.

However, since the electroactive materials currently in use have no electrical topological features of natural extracellular matrix fiber network-like, the matching is poor for electrical features and natural extracellular matrix features and thus the restoration effect of materials is limited.

Content of Invention

With respect to such technical problems with materials as poor matching of natural extracellular matrix characteristics and limited restoration effect of materials, the invention provides a kind of electrified composite membrane with extracellular matrix electrical topology characteristics and its preparation method.

Thus, the invention provides a kind of electrified composite membrane with extracellular matrix electrical topology characteristics, which is composed of high polymers and piezoelectric fiber fillings.

Preferentially, the material of high polymers is a kind or compound of ferroelectric high polymer polyvinylidene fluoride (PVDF) or polyvinylidene fluoride-trifluoroethylene (P (VDF-TrFE));

Preferentially, piezoelectric fiber fillings are piezoelectric active fiber materials. The said piezoelectric active fiber materials are a kind or multi-compound of barium titanate fiber, zinc oxide fiber and KNN fiber.

Preferentially, the said electrified composite membrane is a thin film material and the said electrified composite membrane has a thickness of 10 μm~500 μm.

Preferentially, the said electrified composite membrane with extracellular matrix electrical topology characteristics is a kind of thin-film-shape material with a film thickness of 30-300 μm and the volume fraction of barium titanate fiber in electrified composite membrane is 5-15 vol %.

As for the preparation method of electrified composite membrane with extracellular matrix electrical topology characteristics as mentioned in the invention, the composite filming process of the said ferroelectric polymer matrix and piezoelectric fiber fillings is completed by pouring or casting, particularly in the following steps:

(1) Take a certain amount of glacial acetic acid and acetylacetone for mixing evenly, stirring for 5 min, prepare the mixed solvent of glacial acetic acid and acetylacetone, add barium acetate into the mixed solvent of glacial acetic acid and acetylacetone, stir for 1 h, add tetrabutyl titanate with the same molar weight as barium acetate, stir for 15 min, then add in polyvinylpyrrolidone, with the mass ratio of 9:32 with as barium acetate, and stir for 3 h;

(2) Prepare Barium Titanate Nanofiber

Inject into the injector the mixed solvent obtained in Step (1), and obtain barium titanate nanofiber with the diameter of 50 nm-500 nm, with the static electrospinning technology under a voltage of 10 kV~16 kV;

(3) Add the barium titanate nanofiber obtained in Step (2) into 0.01~0.1 mol/L of dopamine aqueous solution to form the solution with a concentration range of 0.01~0.1 g/mL stir for 6 h~12 h at a temperature of 40° C.~80° C., then apply ultrasonic concussion for 1 min~15 min, centrifugal washing for 3~5 times, and then ultrasonic concussion for 1~10 min with a power of 180 W, to obtain barium titanate nanofiber fillings with a draw ratio of 8~20;

(4) Take barium titanate nanofiber fillings obtained in Step (3), add into the organic solvent, apply ultrasonic concussion and stir for 1 h~3 h to obtain the fiber filling dispersion liquid. The organic solvent is selected from N—N-dimethylformamide (DMF). The mass percent of fiber filling obtained in this step is 1.5%~30%.

(5) Weigh and take ferroelectric high polymers, add into the organic solvent DMF, stir for 3 h~6 h till completely solved to obtain the polymer solution. The concentration of solution obtained is 0.14 g/ml. The said ferroelectric high polymer is P (VDF-TrFE) or PVDF.

(6) Add the dispersion liquid obtained in Step (4) into the polymer solution obtained in Step (5) so that the volume fraction range of barium titanate fiber fillings in polymer matrix is 1~20 vol %, stir for 6 h~12 h so that the fiber fillings are evenly dispersed in polymer matrix to obtain the polymer mixed liquid containing ceramic fiber filling;

(7) Take mixed liquid obtained in Step (6) for casting in the casting machine, place the cast film obtained under a temperature of 40° C.~100° C. for drying to obtain a kind of composite film material with a thickness of 10 μm~500 μm;

(8) Polarize the film material obtained in Step (7), as per parameters: 1 kV~30 kV (voltage), 0 mm~50 mm (distance), 25° C.~150° C. (temperature) and 1 min~60 min (time), to obtain a kind of electrified composite membrane with extracellular matrix electrical topology characteristics Preferentially, in the mixed solvent of glacial acetic acid and acetylacetone as mentioned in Step (1), the volume ratio of glacial acetic acid and acetylacetone is 9:1.34 ml/g.

Preferentially, the feeding volume ratio of barium acetate and glacial acetic acid in Step (1) is 1.703:9 g/ml.

Due to their inherent spontaneous popularizing performance and biocompatibility, such ferroelectric polymers as Polyvinylidene fluoride (PVDF) and polyvinylidene fluoride-trifluoroethylene (P(VDF-TrFE)) are currently applied widely in the field of biomedical research. Additionally, due to their good flexibility and workability, they have the good clinical operability and become currently the main source of electriferous biomedical materials. In order to make the materials to have the network-like electrical topological features of natural EXTRACELLULAR MATRIX fiber, the invention mix in the piezoelectric ceramic barium titanate nanofiber irregularly for electrical adaptation of materials with cells/tissues.

The beneficial effects of this invention are:

With respect to the deficiency of the existing technologies, the invention provides a kind of electrified composite membrane with extracellular matrix electrical topology characteristics and the method of its preparation.

(1) Since the invention uses ferroelectric polymer and piezoelectric active fiber filling as the main component, the film materials formed have an even structure, anisotropy in distribution of fiber fillings and stable performance, with good flexibility and high clinical operability, for the details of which see FIG. 1 and FIG. 2.

(2) Due to their inherent spontaneous polarizing feature, the film materials prepared in the invention can be polarized so that the film material surface has certain polarization charge and can maintain electrical stability. Furthermore, due to the structural features and potential distribution characteristics of fiber fillings, the composite film surface has the natural extracellular matrix has the electrical topological features. For details, see FIG. 3 and FIG. 4

(3) Upon being implanted in bone defects, the electrified composite membrane materials made in the invention perform well in inducing bone restoration. For details, see FIG. 6.

(4) The preparation process used in the invention is simply, with relatively high yield and high operability and can be industrialized.

All in all, a kind of electrified composite membrane with extracellular matrix electrical topology characteristics provided by the invention performs well in terms of macro performance as well as micro structure. In the process of bone restoration, it not only can compensate an appropriate electrical micro-environment for bone defects, but also can form a proper electrical adaptation with host cells and tissues, promoting the generation of new bones, without causing tissue adhesion to avoid any residual of materials for dual improvement in clinical applicability and induction of osteogenic adaptation.

DESCRIPTIONS OF FIGURES

PARTICULAR IMPLEMENTING MODE

With the following example, the invention can be better understood. However, the technicians of the field may understand easily that the content prescribed in the example is used to explain the invention only and neither shall nor will limit the invention as prescribed in the Claims.

Example 1

Figure 1:
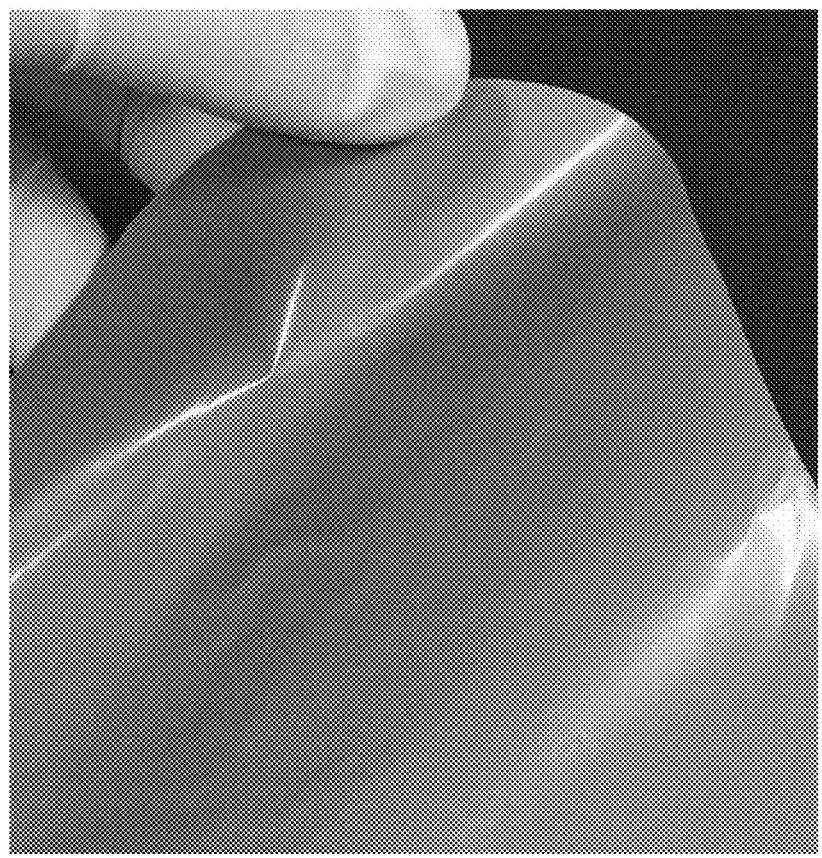
FIG. 1 is a photo of electrified composite membrane with extracellular matrix electrical topology characteristics prescribed in Example 1.
Figure 2:
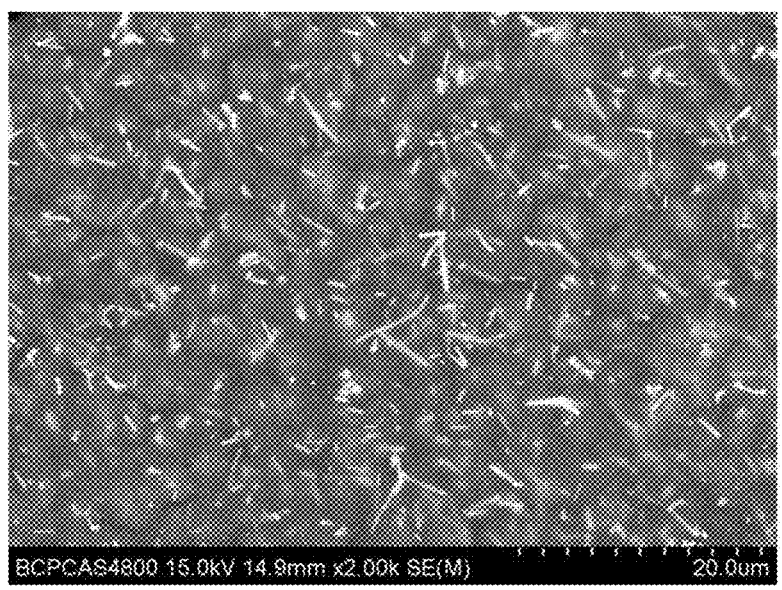
FIG. 2 is a surface SEM photo of electrified composite membrane with extracellular matrix electrical topology characteristics as prescribed in Example 1.
Figure 3:
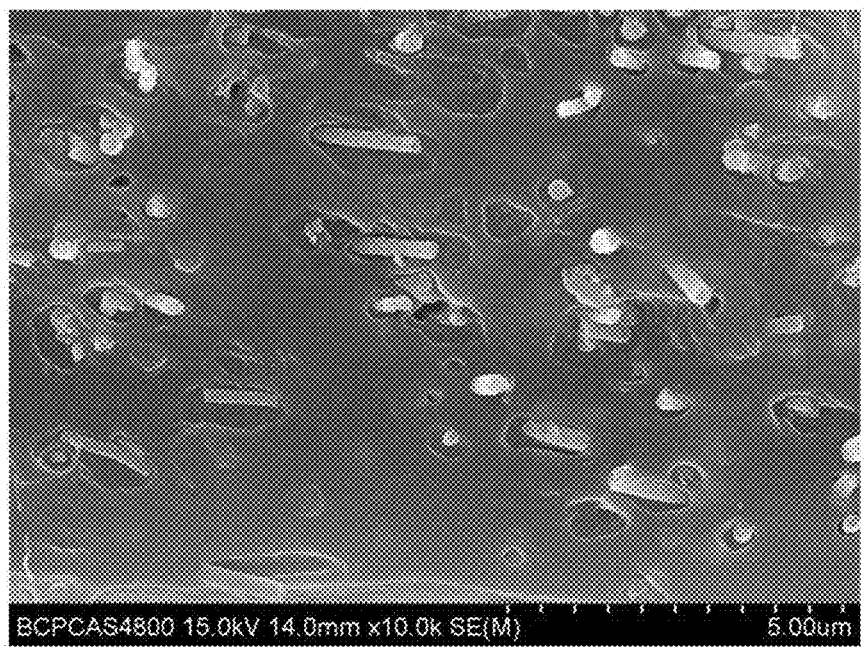
FIG. 3 is a section SEM photo of electrified composite membrane with extracellular matrix electrical topology characteristics as prescribed in Example 1.

(1) Take 9 ml of glacial acetic acid and 1.340 g of acetylacetone, mix and stir for 5 min before adding 1.703 g of barium acetate, stirring for 1 h, adding 2.266 g of tetrabutyl titanate, stirring for 15 min, then adding 0.45 g of polyvinylpyrrolidone (PVP), stirring for 3 h;

(2) Inject into the injector the mixed solvent obtained in Step (1), and obtain barium titanate nanofiber with the diameter of 200 nm, with the static electrospinning technology under a voltage of 14 kV;

(3) Add the barium titanate nanofiber obtained in Step (2) into 0.01 mol/L of dopamine aqueous solution for bathing in water of 60 degrees, heating and stirring for 12 h, then apply ultrasonic concussion for 5 min, centrifugal drying to obtain barium titanate nanofiber fillings with a draw ratio of 12;

(4) Take an appropriate amount of barium titanate nanofiber fillings obtained in Step (3) for ultrasonic oscillation dispersion in 3 mL of organic solvent DMF, apply ultrasonic oscillation and stir for 1.5 h to obtain the fiber filling, dispersion liquid;

(5) Weigh and take 1 g of P (VDF-TrFE), add in 7 mL of organic solvent DMF, and stir for 5 h till completed solved to obtain P (VDF-TrFE) solution;

(6) Add the dispersion liquid obtained in Step (4) in P(VDF-TrFE) solution obtained in Step (5) so that the volume fraction of barium titanate fiber fillings in polymer is 7 vol %, stir for 10 h so that barium titanate fiber fillings are evenly dispersed in P (VDF-TrFE) matrix to obtain the mixed liquid;

(7) Take the mixed liquid obtained in Step (6) for casting in the casting machine, place the cast film obtained under a temperature of 55° C. for drying so that the solvent is completely evaporated to obtain a kind of composite film material with a thickness of 30 μm;

(8) Polarize the film material obtained in Step (7), as per parameters: 20 kV (voltage), 20 mm (distance), 25° C. (temperature) and 30 min (time), to obtain a kind of electrified composite membrane with extracellular matrix electrical topology characteristics Its main components are P (VDF-TrFE) and barium titanate nanofiber, as the thin-film material with a thickness of 30 μm. The volume fraction of barium titanate fiber fillings in electrified composite membrane is 5 vol %. For the photo the product in the example, see FIG. 1. For the surface SEM photo, see FIG. 2. For the section SEM photo, see FIG. 3.

Figure 4:
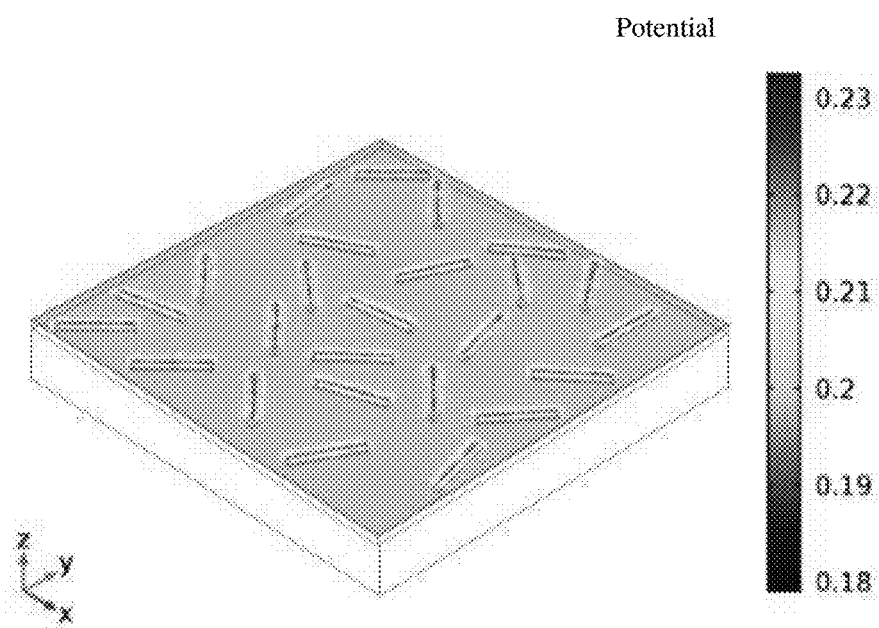
FIG. 4 is the electrical stability result of electrified composite membrane with extracellular matrix electrical topology characteristics as prescribed in Example 1.

Product Performance Testing:

(1) With COMSOL software, simulate and analyze the potential distribution features of the film material surface. For the results of simulation and analysis, see FIG. 4.

Figure 5:
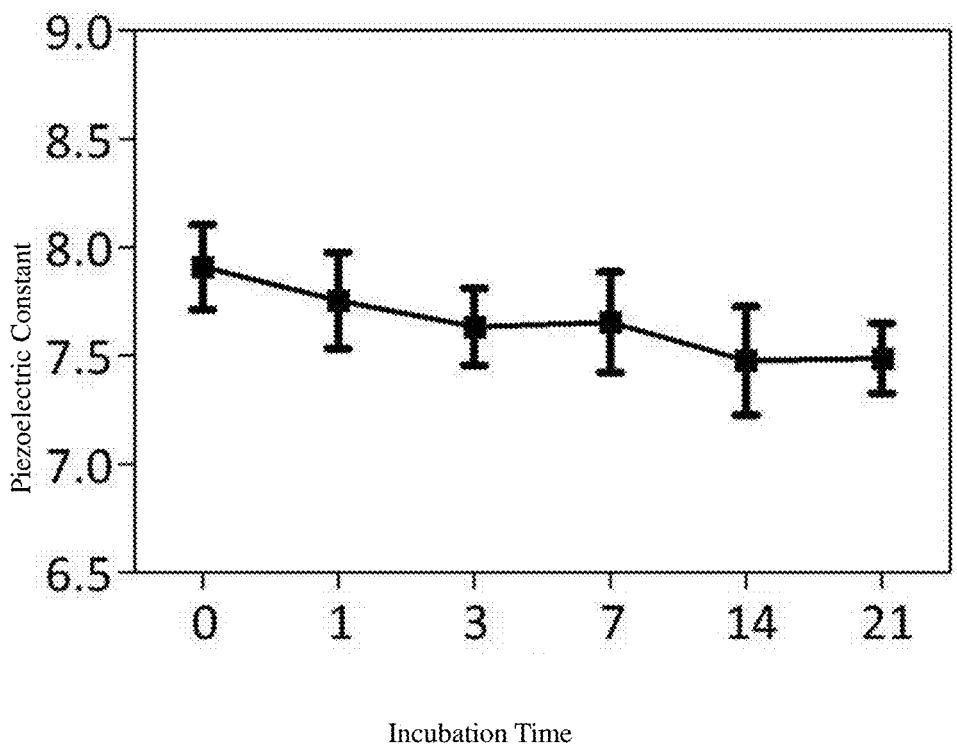
FIG. 5 is the analytical result of surface potential distribution simulation of electrified composite membrane with extracellular matrix electrical topology characteristics as prescribed in Example 1.

(2) Place the film material obtained in Step (8) in serum-free medium, for incubation for 0, 1, 3, 7, 14 and 21 days respectively under the condition of 37° C. At each time point, take out the material for piezoelectric constant testing. For the test result, see FIG. 5.

Figure 6:
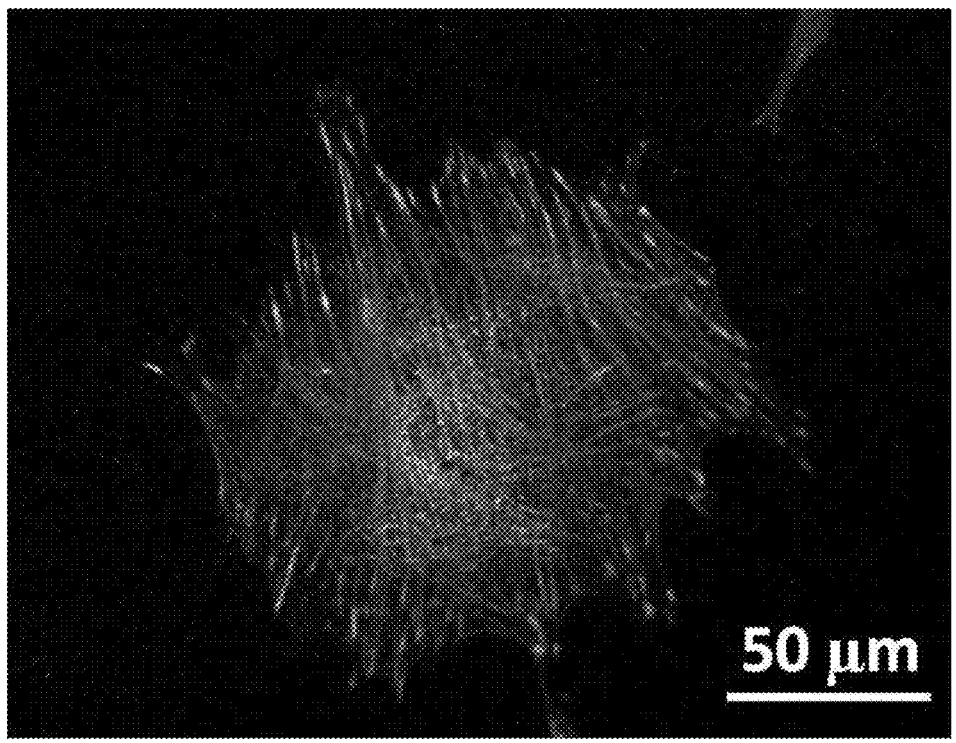
FIG. 6 is a LSCM photo of adhesion and spreading out 12 hours after the electrified composite membrane with extracellular matrix electrical topology characteristics acts on Rat BM MSC as prescribed in Example 1.

(3) Sterilize the film material obtained in (8) with Cobalt-60, then vaccinate, on its top, RMSC with a density of $5\times10^4$, for incubation for 12 hours in total before immunostaining fixed and adherent plagues and then observing with LSCM. For the test result, see FIG. 6.

Figure 7:
FIG. 7 is a Micro-CT photo of the test set and reference set of the experiment for the electrified composite membrane to restore rat skull defect as prescribed in Example 1.

(4) Upon sterilizing with Cobalt-60, cut the film material obtained in Step (8) into a circular diaphragm with a diameter of 8 mm, for covering the rat skull defect with a diameter of 5 mm, while the defect not covered with any material is taken as the reference set. 4 weeks after the surgery, kill the animal and separate the film material for micro-CT scanning and observation. For the test result, see FIG. 7.

Example 2

(1) Take 9 ml of glacial acetic acid and 1.340 g of acetylacetone, mix and stir for 5 min before adding 1.703 g of barium acetate, stirring for 1 h, adding 2.266 g of tetrabutyl titanate, stirring for 15 min, then adding 0.45 g of polyvinylpyrrolidone (PVP), stirring for 3 h;

(2) Inject into the injector the mixed solvent obtained in Step (1), and obtain barium titanate nanofiber with the diameter of 300 nm, with the static electrospinning technology under a voltage of 16 kV;

(3) Add the barium titanate nanofiber obtained in Step (2) into 0.05 mol/L of dopamine aqueous solution for bathing in water of 60 degrees, heating and stirring for 12 h, then apply ultrasonic concussion for 10 min, centrifugal drying to obtain barium titanate nanofiber fillings with a draw ratio of 8;

(4) Take an appropriate amount of barium titanate nanofiber fillings obtained in Step (3) for ultrasonic oscillation dispersion in 3 mL of organic solvent DMF, apply ultrasonic oscillation and stir for 1.5 h to obtain the fiber filling, dispersion liquid;

(5) Weigh and take 1 g of P (VDF-TrFE), add in 7 mL of organic solvent DMF, and stir for 3 h till completed solved to obtain P (VDF-TrFE) solution;

(6) Add the dispersion liquid obtained in Step (4) in P(VDF-TrFE) solution obtained in Step (5) so that the volume fraction of barium titanate fiber fillings in polymer is 7 vol %, stir for 10 h so that barium titanate fiber fillings are evenly dispersed in P (VDF-TrFE) matrix to obtain the mixed liquid;

(7) Take the mixed liquid obtained in Step (6) for casting in the casting machine, place the cast film obtained under a temperature of 45° C. for drying so that the solvent is completely evaporated to obtain a kind of composite film material with a thickness of 50 μm;

(8) Polarize the film material obtained in Step (7), as per parameters: 15 kV (voltage), 20 mm (distance), 50° C. (temperature) and 60 min (time), to obtain a kind of electrified composite membrane with extracellular matrix electrical topology characteristics Its main components are P (VDF-TrFE) and barium titanate nanofiber, as the thin-film material with a thickness of 30 μm. The volume fraction of barium titanate fiber fillings in electrified composite membrane is 7 vol %.

Product Performance Testing:

(1) With COMSOL software, simulate and analyze the potential distribution features of the film material surface.

(2) Place the film material obtained in Step (8) in serum-free medium, for incubation for 0, 1, 3, 7, 14 and 21 days respectively under the condition of 37° C. At each time point, take out the material for piezoelectric constant testing.

(3) Sterilize the film material obtained in (8) with Cobalt-60, then vaccinate, on its top, RMSC with a density of $5\times10^4$, for incubation for 12 hours in total before immunostaining fixed and adherent plagues and then observing with LSCM.

(4) Upon sterilizing with Cobalt-60, cut the film material obtained in Step (8) into a circular diaphragm with a diameter of 8 mm, for covering the rat skull defect with a diameter of 5 mm, while the defect not covered with any material is taken as the reference set. 4 weeks after the surgery, kill the animal and separate the film material for micro-CT scanning and observation.

Example 3

(1) Take 9 ml of glacial acetic acid and 1.340 g of acetylacetone, mix and stir for 5 min before adding 1.703 g of barium acetate, stirring for 1 h, adding 2.266 g of tetrabutyl titanate, stirring for 15 min, then adding 0.45 g of polyvinylpyrrolidone (PVP), stirring for 3 h;

(2) Inject into the injector the mixed solvent obtained in Step (1), and obtain barium titanate nanofiber with the diameter of 400 nm, with the static electrospinning technology under a voltage of 12 kV;

(3) Add the barium titanate nanofiber obtained in Step (2) into 0.08 mol/L of dopamine aqueous solution for bathing in water of 60 degrees, heating and stirring for 12 h, then apply ultrasonic concussion for 10 min, centrifugal drying to obtain barium titanate nanofiber fillings with a draw ratio of 20;

(4) Take an appropriate amount of barium titanate nanofiber fillings obtained in Step (3) for ultrasonic oscillation dispersion in 3 mL of organic solvent DMF, apply ultrasonic oscillation and stir for 1.5 h to obtain the fiber filling, dispersion liquid;

(5) Weigh and take 1 g of P (VDF-TrFE), add in 7 mL of organic solvent DMF, and stir for 5 h till completed solved to obtain P (VDF-TrFE) solution;

(6) Add the dispersion liquid obtained in Step (4) in P(VDF-TrFE) solution obtained in Step (5) so that the volume fraction of barium titanate fiber fillings in polymer is 10 vol %, stir for 10 h so that barium titanate fiber fillings are evenly dispersed in P (VDF-TrFE) matrix to obtain the mixed liquid;

(7) Take the mixed liquid obtained in Step (6) for casting in the casting machine, place the cast film obtained under a temperature of 80° C. for drying so that the solvent is completely evaporated to obtain a kind of composite film material with a thickness of 100 μm;

(8) Polarize the film material obtained in Step (7), as per parameters: 10 kV (voltage), 15 mm (distance), 100° C. (temperature) and 40 min (time), to obtain a kind of electrified composite membrane with extracellular matrix electrical topology characteristics Its main components are P (VDF-TrFE) and barium titanate nanofiber, as the thin-film material with a thickness of 100 μm. The volume fraction of barium titanate fiber fillings in electrified composite membrane is 10 vol %.

Product Performance Testing:

(1) With COMSOL software, simulate and analyze the potential distribution features of the film material surface.

(2) Place the film material obtained in Step (8) in serum-free medium, for incubation for 0, 1, 3, 7, 14 and 21 days respectively under the condition of 37° C. At each time point, take out the material for piezoelectric constant testing.

(3) Sterilize the film material obtained in (8) with Cobalt-60, then vaccinate, on its top, RMSC with a density of $5\times10^4$, for incubation for 12 hours in total before immunostaining fixed and adherent plagues and then observing with LSCM.

(4) Upon sterilizing with Cobalt-60, cut the film material obtained in Step (8) into a circular diaphragm with a diameter of 8 mm, for covering the rat skull defect with a diameter of 5 mm, while the defect not covered with any material is taken as the reference set. 4 weeks after the surgery, kill the animal and separate the film material for micro-CT scanning and observation.

Example 4

(1) Take 9 ml of glacial acetic acid and 1.340 g of acetylacetone, mix and stir for 5 min before adding 1.703 g of barium acetate, stirring for 1 h, adding 2.266 g of tetrabutyl titanate, stirring for 15 min, then adding 0.45 g of polyvinylpyrrolidone (PVP), stirring for 3 h;

(2) Inject into the injector the mixed solvent obtained in Step (1), and obtain barium titanate nanofiber with the diameter of 400 nm, with the static electrospinning technology under a voltage of 12 kV;

(3) Add the barium titanate nanofiber obtained in Step (2) into 0.09 mol/L of dopamine aqueous solution for bathing in water of 60 degrees, heating and stirring for 12 h, then apply ultrasonic concussion for 10 min, centrifugal drying to obtain barium titanate nanofiber fillings with a draw ratio of 20;

(4) Take an appropriate amount of barium titanate nanofiber fillings obtained in Step (3) for ultrasonic oscillation dispersion in 3 mL of organic solvent DMF, apply ultrasonic oscillation and stir for 1.5 h to obtain the fiber filling, dispersion liquid;

(5) Weigh and take 1 g of P (VDF-TrFE), add in 7 mL of organic solvent DMF, and stir for 5 h till completed solved to obtain P (VDF-TrFE) solution;

(6) Add the dispersion liquid obtained in Step (4) in P(VDF-TrFE) solution obtained in Step (5) so that the volume fraction of barium titanate fiber fillings in polymer is 10 vol %, stir for 10 h so that barium titanate fiber fillings are evenly dispersed in P (VDF-TrFE) matrix to obtain the mixed liquid;

(7) Take the mixed liquid obtained in Step (6) for casting in the casting machine, place the cast film obtained under a temperature of 80° C. for drying so that the solvent is completely evaporated to obtain a kind of composite film material with a thickness of 100 μm;

(8) Polarize the film material obtained in Step (7), as per parameters: 10 kV (voltage), 15 mm (distance), 100° C. (temperature) and 40 min (time), to obtain a kind of electrified composite membrane with extracellular matrix electrical topology characteristics Its main components are P (VDF-TrFE) and barium titanate nanofiber, as the thin-film material with a thickness of 120 μm. The volume fraction of barium titanate fiber fillings in electrified composite membrane is 10 vol %.

Product Performance Testing:

(1) With COMSOL software, simulate and analyze the potential distribution features of the film material surface.

(2) Place the film material obtained in Step (8) in serum-free medium, for incubation for 0, 1, 3, 7, 14 and 21 days respectively under the condition of 37° C. At each time point, take out the material for piezoelectric constant testing.

(3) Sterilize the film material obtained in (8) with Cobalt-60, then vaccinate, on its top, RMSC with a density of $5\times10^4$, for incubation for 12 hours in total before immunostaining fixed and adherent plagues and then observing with LSCM.

(4) Upon sterilizing with Cobalt-60, cut the film material obtained in Step (8) into a circular diaphragm with a diameter of 8 mm, for covering the rat skull defect with a diameter of 5 mm, while the defect not covered with any material is taken as the reference set. 4 weeks after the surgery, kill the animal and separate the film material for micro-CT scanning and observation.

Example 5

(1) Take 9 ml of glacial acetic acid and 1.340 g of acetylacetone, mix and stir for 5 min before adding 1.703 g of barium acetate, stirring for 1 h, adding 2.266 g of tetrabutyl titanate, stirring for 15 min, then adding 0.45 g of polyvinylpyrrolidone (PVP), stirring for 3 h;

(2) Inject into the injector the mixed solvent obtained in Step (1), and obtain barium titanate nanofiber with the diameter of 500 nm, with the static electrospinning technology under a voltage of 10 kV;

(3) Add the barium titanate nanofiber obtained in Step (2) into 0.1 mol/L of dopamine aqueous solution for bathing in water of 60 degrees, heating and stirring for 12 h, then apply ultrasonic concussion for 15 min, centrifugal drying to obtain barium titanate nanofiber fillings with a draw ratio of 8;

(4) Take an appropriate amount of barium titanate nanofiber fillings obtained in Step (3) for ultrasonic oscillation dispersion in 3 mL of organic solvent DMF, apply ultrasonic oscillation and stir for 1.5 h to obtain the fiber filling, dispersion liquid;

(5) Weigh and take 1 g of P (VDF-TrFE), add in 7 mL of organic solvent DMF, and stir for 5 h till completed solved to obtain P (VDF-TrFE) solution;

(6) Add the dispersion liquid obtained in Step (4) in P(VDF-TrFE) solution obtained in Step (5) so that the volume fraction of barium titanate fiber fillings in polymer is 15 vol %, stir for 10 h so that barium titanate fiber fillings are evenly dispersed in P (VDF-TrFE) matrix to obtain the mixed liquid;

(7) Take the mixed liquid obtained in Step (6) for casting in the casting machine, place the cast film obtained under a temperature of 100° C. for drying so that the solvent is completely evaporated to obtain a kind of composite film material with a thickness of 300 μm;

(8) Polarize the film material obtained in Step (7), as per parameters: 30 kV (voltage), 50 mm (distance), 150° C. (temperature) and 10 min (time), to obtain a kind of electrified composite membrane with extracellular matrix electrical topology characteristics Its main components are P (VDF-TrFE) and barium titanate nanofiber, as the thin-film material with a thickness of 300 μm. The volume fraction of barium titanate fiber fillings in electrified composite membrane is 15 vol %.

Product Performance Testing:

(1) With COMSOL software, simulate and analyze the potential distribution features of the film material surface.

(2) Place the film material obtained in Step (8) in serum-free medium, for incubation for 0, 1, 3, 7, 14 and 21 days respectively under the condition of 37° C. At each time point, take out the material for piezoelectric constant testing.

(3) Sterilize the film material obtained in (8) with Cobalt-60, then vaccinate, on its top, RMSC with a density of $5\times10^4$, for incubation for 12 hours in total before immunostaining fixed and adherent plagues and then observing with LSCM.

(4) Upon sterilizing with Cobalt-60, cut the film material obtained in Step (8) into a circular diaphragm with a diameter of 8 mm, for covering the rat skull defect with a diameter of 5 mm, while the defect not covered with any material is taken as the reference set. 4 weeks after the surgery, kill the animal and separate the film material for micro-CT scanning and observation. For the product performance test results of Examples 2~5, refer to Example 1.

What is claimed is:

1. A preparation method for an electrified composite membrane with extracellular matrix electrical topology characteristics for inducing bone restoration, wherein said electrified composite membrane is composed of ferroelectric high polymer and piezoelectric fiber filling, and wherein said electrified composite membrane is prepared by dispersing, solving and casting with organic solvent, in the following steps:
   (1) evenly mix glacial acetic acid and acetylacetone, stirring for 5 min, add barium acetate into the mixed solvent of glacial acetic acid and acetylacetone, stir for 1 h, add tetrabutyl titanate with the same molar weight as barium acetate, stir for 15 min, then add in polyvinylpyrrolidone with barium acetate in a mass ratio of 9:32, and stir for 3 h;
   (2) inject the mixed solvent obtained in Step (1) into an injector, and obtain barium titanate nanofiber with the diameter of 50 nm-500 nm with the static electrospinning technology under a voltage of 10 kV-16 kV;
   (3) add the barium titanate nanofiber obtained in Step (2) into 0.01-0.1 mol/L of dopamine aqueous solution to form the solution with a concentration range of 0.01~0.1 g/mL, stir for 6 h-12 h at a temperature of 40° C.-80° C., then apply ultrasonic vibration for 1 min~15 min, centrifugal washing for 3-5 times, and then ultrasonic vibration for 1-10 min with a power of 180 W, to obtain barium titanate nanofiber fillings with a draw ratio of 8-20;
   (4) use the barium titanate nanofiber fillings obtained in Step (3), add into an organic solvent, N—N-dimethylformamide, apply ultrasonic vibration and stir for 1 h-3 h to obtain a fiber filling dispersion liquid;
   (5) measure a certain amount of ferroelectric high polymers to add into an organic solvent N—N-dimethylformamide, stir for 3 h-6 h till completely dissolved to obtain the polymer solution, wherein the concentration of the solution is 0.14 g/ml, and wherein the ferroelectric high polymer is polyvinylidene fluoride or polyvinylidene fluoride-trifluoroethylene;
   (6) add the dispersion liquid obtained in Step (4) into the polymer solution obtained in Step (5) so that the volume fraction range of barium titanate fiber fillings in polymer matrix is 1-20 vol %, stir for 6 h~12 h so that the fiber fillings are evenly dispersed in polymer matrix to obtain a polymer mixed liquid containing ceramic fiber filling;
   (7) use the polymer mixed liquid obtained in Step (6) for casting in a casting machine, place the obtained cast film under a temperature of 40° C.-100° C. for drying to generate a composite film material with a thickness of 10 μm-500 μm;
   (8) polarize the composite film material obtained in Step (7), under the following polarizing parameters: 1 kV~30 kV (voltage), 0 mm~50 mm (distance), 25° C.-150° C. (temperature) and 1 min~60 min (time), to obtain an electrified composite membrane with extracellular matrix electrical topology characteristics; and
   (9) use the electrified composite membrane with extracellular matrix electrical topology characteristics to induce bone restoration.

2. The preparation method of electrified composite membrane of claim 1 for inducing bone restoration is featured for that in the mixed solvent of glacial acetic acid and acetylacetone as mentioned in in Step (1), the ratio of glacial acetic acid and acetylacetone is 9 ml:1.34 g.

3. The preparation method of electrified composite membrane of claim 1 for inducing bone restoration, wherein feeding ratio of barium acetate and glacial acetic acid in Step (1) is 1.703 g:9 ml.

4. The preparation method of electrified composite membrane of claim 1 for inducing bone restoration, wherein mass percentage of fiber fillings obtained in Step (4) in the organic solvent is 1.5%-30%.

* * * * *